United States Patent
Ma et al.

(10) Patent No.: US 8,814,852 B2
(45) Date of Patent: *Aug. 26, 2014

(54) APPARATUS AND METHOD FOR COOLING AND MOVING ABLATION ELEMENTS

(71) Applicant: St. Jude Medical, Atrial Fibrillation Division, Inc., St. Paul, MN (US)

(72) Inventors: Zhenyi Ma, San Jose, CA (US); Gleb V. Klimovitch, Santa Clara, CA (US); John W. Sliwa, Los Altos Hills, CA (US)

(73) Assignee: St. Jude Medical, Atrial Fibrillation Division, Inc., St. Paul, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/045,446

(22) Filed: Oct. 3, 2013

(65) Prior Publication Data
US 2014/0031806 A1    Jan. 30, 2014

Related U.S. Application Data

(63) Continuation of application No. 13/593,161, filed on Aug. 23, 2012, now Pat. No. 8,551,087, which is a continuation of application No. 11/961,483, filed on Dec. 20, 2007, now Pat. No. 8,267,930.

(51) Int. Cl.
*A61B 18/14* (2006.01)
*A61B 18/00* (2006.01)

(52) U.S. Cl.
CPC .............. *A61B 18/14* (2013.01); *A61B 18/1492* (2013.01); *A61B 2018/0016* (2013.01); *A61B 2018/00351* (2013.01); *A61B 2018/00577* (2013.01); *A61B 2018/141* (2013.01); *A61B 2018/1467* (2013.01)
USPC ............................................... 606/27; 606/28

(58) Field of Classification Search
CPC .............. A61B 18/14; A61B 18/1402; A61B 18/1442; A61B 18/1492; A61B 2018/0016; A61B 2018/00166; A61B 2018/00184; A61B 2018/00214; A61B 2018/00345; A61B 2018/00351; A61B 2018/00577; A61B 2018/141; A61B 2018/1467
USPC ............................... 606/27, 28, 41–42, 48–50
See application file for complete search history.

(56) References Cited

U.S. PATENT DOCUMENTS 6,971,394 B2 * 12/2005 Sliwa et al. ................... 128/898

* cited by examiner

*Primary Examiner* — Linda Dvorak
*Assistant Examiner* — Amanda Scott
(74) *Attorney, Agent, or Firm* — Dykema Gossett PLLC

(57) ABSTRACT

A medical device comprising a cell including an ablation element and a carrier configured to receive at least a portion of said ablation element is disclosed. The medical device further comprises a tube enclosing the cell. At least a portion of the tube includes a membrane and the tube includes at least one hole proximate the ablation element for facilitating fluid flow. The medical device further comprises a fluid inlet for providing fluid to the interior of the tube. A method of using the medical device is also disclosed.

20 Claims, 4 Drawing Sheets

APPARATUS AND METHOD FOR COOLING AND MOVING ABLATION ELEMENTS

CROSS-REFERENCE TO RELATED APPLICATIONS

This application is a continuation of pending U.S. application Ser. No. 13/593,161, filed Aug. 23, 2012 ("the '161 application"), which is a continuation of U.S. application Ser. No. 11/961,483, filed Dec. 20, 2007 ("the '483 application"), now issued as U.S. Pat. No. 8,267,930 ("the '930 patent"). The '161 application, '483 application, and '930 patent are hereby incorporated by reference in their entireties as though fully set forth herein.

BACKGROUND OF THE INVENTION a. Field of the Invention

The invention is directed toward an apparatus and method for cooling and moving ablation elements in a medical device.

b. Background Art

In a normal heart, contraction and relaxation of the heart muscle (myocardium) takes place in an organized fashion as electrochemical signals pass sequentially through the myocardium from the sinoatrial (SA) node located in the right atrium to the atrialventricular (AV) node and then along a well defined route which includes the His-Purkinje system into the left and right ventricles. Atrial fibrillation results from disorganized electrical activity in the heart muscle, or myocardium. An increasingly common medical procedure for the treatment of certain types of cardiac arrhythmia and atrial arrhythmia involves the ablation of tissue in the heart to cut off the path for stray or improper electrical signals.

Ablation may be performed either from within the chambers of the heart (endocardial ablation) using endovascular devices (e.g., catheters) introduced through arteries or veins, or from outside the heart (epicardial ablation) using devices introduced into the chest. The ablation devices are used to create elongated transmural lesions—that is, lesions extending through a sufficient thickness of the myocardium to block electrical conduction—which form the boundaries of the conductive corridors in the atrial myocardium. The ablation devices create lesions at particular points in the cardiac tissue by physical contact of the cardiac tissue with an ablation element and the application of energy.

One challenge in obtaining an adequate ablation lesion is the constant movement of the heart, especially when there is an erratic or irregular heart beat. Another difficulty in obtaining an adequate ablation lesion is retaining sufficient and uniform contact with the cardiac tissue across the entire length of the ablation element surface. Without sufficiently continuous and uniform contact, the associated ablation lesions may not be adequate.

An epicardial ablation device may be used to create uniform, continuous, linear lesions during cardiac ablation. The device (e.g., belt) may comprise a plurality of cells connected together by a hinge wire. The hinge wire may comprise nylon or metal and may be provided to connect the cells together so that they are configured to form a substantially complete ring for generally encircling the cardiac tissue at the time of ablation. Each cell may comprise an ablation element, as well as a cell carrier for retaining the ablation element. The device may be positioned securely around a patient's atrium while the ablation elements apply energy (e.g., high intensity focused ultrasound energy) to the targeted tissue. In a conventional epicardial ablation device, the cells typically must be placed as closely together as possible in order to minimize possible ablation gaps between cells. However, the close placement of cells may negatively affect the mechanical flexibility of the device.

In a conventional epicardial ablation device, a membrane is disposed in front of the emitting surface of each ablation element and connected to each cell carrier. Each cell is separately and hermetically sealed with its own designated membrane. Each membrane is generally provided to conform to the required shape to fill a gap between the ablation element and the tissue to be ablated. Each membrane may be fed by an individual fluid inlet leading to the membrane that provides a fluid, such as saline, to the membrane interface. The fluid may flow in the opening between the emitting surface of the ablation element and the membrane in order to provide good acoustic contact, with independent fluid flow in the front and lateral sides of each cell. Multiple fluid inlets are required for the device (i.e., an individual fluid inlet for each cell), which may increase cost and assembly time for the device.

The ablation elements also require cooling in front of the emitting surfaces of the ablation elements. A fluid, such as saline, may serve as a coolant. In addition to flowing in an opening between the emitting surface of each ablation element and the inner surface of each membrane, the fluid may also flow through holes in each membrane (e.g., holes formed by lasers) toward the outer surface of the membrane.

BRIEF SUMMARY OF THE INVENTION

It is desirable to improve the reliability and efficiency of the ablation device by increasing the flow rate of the coolant fluid proximate the ablation elements, so that the coolant circulates more quickly among the cells of the device to provide for more uniform contact between the device and the surface of the tissue to be ablated.

It is also desirable to reduce the profile of the device and decrease assembly time and costs by eliminating the use of a separate fluid tube for each cell of the device, eliminating the use of a separate membrane that must be sealed to each cell, reducing the number of pressure and/or flow sensors necessary to detect a malfunction within the device, and/or reducing the overall number of cells within the device necessary to perform tissue ablation.

It is also desirable to improve the mechanical flexibility of the device without sacrificing the ability to create uniform, continuous, linear lesions during cardiac ablation.

Thus, there remains a desire for a medical device for tissue ablation that is more reliable and efficient; provides a reduced profile, decreased assembly time, and reduced cost; and/or has improved mechanical flexibility.

A medical device comprising a cell including an ablation element and a carrier configured to receive at least a portion of said ablation element is disclosed. The medical device further comprises a tube enclosing the cell. At least a portion of the tube includes a membrane and the tube includes at least one hole proximate the ablation element for facilitating fluid flow. The medical device further comprises a fluid inlet for providing fluid to the interior of the tube. A method of using the medical device is also disclosed.

The foregoing and other aspects, features, details, utilities, and advantages of the present invention will be apparent from reading the following description and claims, and from reviewing the accompanying drawings.

DETAILED DESCRIPTION OF THE INVENTION

Figure 1:
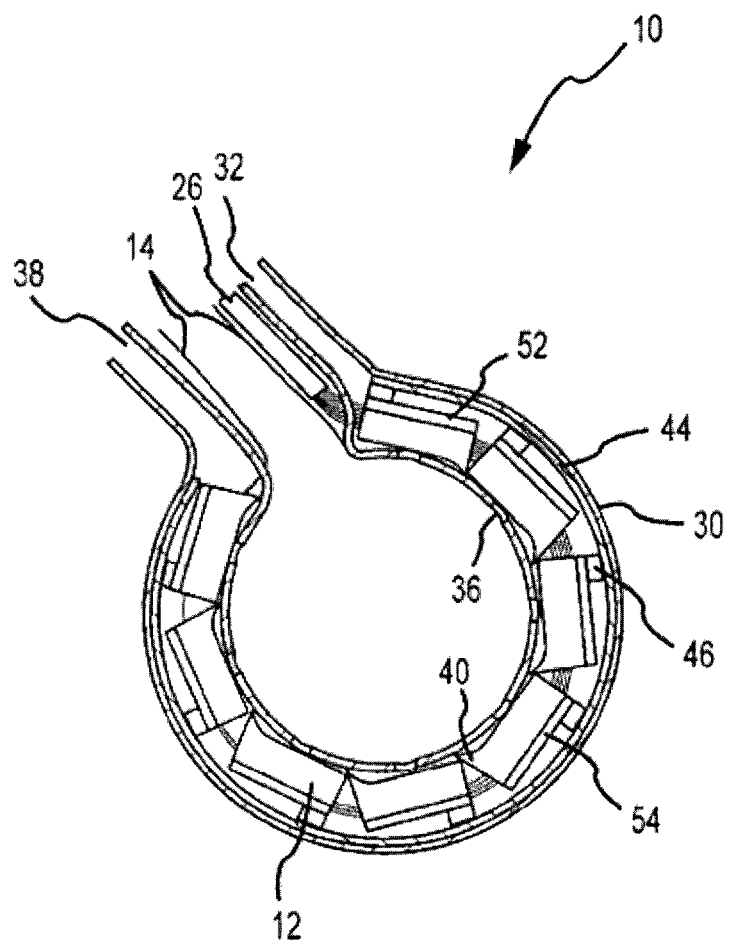
FIG. 1 is a cross-sectional view of a device in accordance with an embodiment of the invention.

Referring to FIG. 1, an epicardial ablation device 10 is illustrated. Related devices have been previously described in U.S. Pat. Nos. 6,237,605; 6,314,962; 6,929,010; and 7,052,493 and U.S. Patent Application Publication No. 2003/0069574, which are hereby incorporated by reference as though fully set forth herein. Device 10 may comprise a plurality of cells 12 at a first end. The cells 12 may be arranged in series and may comprise an assembly. The assembly of cells may be configured to curve and form a substantially complete ring, as illustrated in FIG. 1. The assembly of cells may also be configured to form a number of other shapes useful for various applications. The cells may be positioned adjacent each other so as to promote sufficient movement to allow for shaping of device 10. Adjacent cells 12 may be connected to a hinge wire 14 that is provided so that the plurality of cells may be configured into one or more shapes or formations, such as a substantially complete ring. Hinge wire 14 may comprise nylon or metal and may be used to connect the cells in series. The ends of device 10 may be connected (e.g., locked) to each other to encircle at least a portion of the heart (e.g., the pulmonary veins) to create a substantially continuous lesion. Although the device has been described in connection with creating a continuous lesion around the pulmonary veins, the device may also be used for creating other lesions beneficial in treating electrophysiological conditions (e.g., ablating partially around the pulmonary veins or at other locations). Moreover, such devices are not limited to creating lesions completely around the pulmonary veins.

Figure 2:
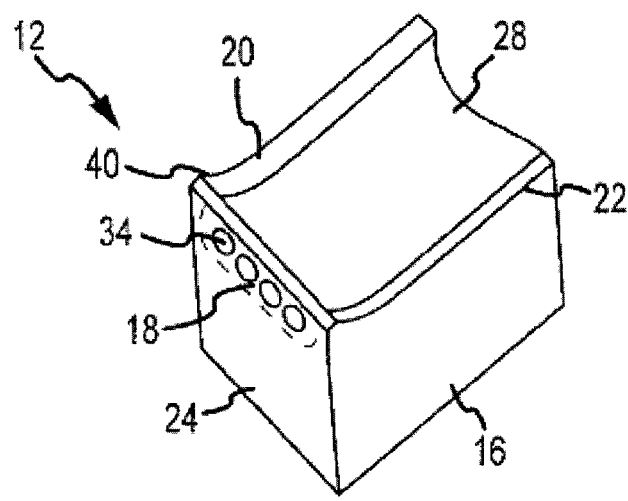
FIG. 2 is a perspective view of a cell carrier without a membrane for the device of FIG. 1 in accordance with an embodiment of the invention.

Referring now to FIG. 2, each cell 12 may comprise a self-sealed unit which may comprise a cell carrier 16 with an ablation element 18. Cell 12 generally refers to a unit with a single ablation element 18. Carrier 16 may comprise molded plastic. Carrier 16 may include a plurality of passive walls (e.g., walls that are not acoustically active). Carrier 16 may include a pair of side walls 20, 22, and an upper wall 24 connected therebetween. A top surface of the upper wall may include one or more formations or protrusions (not shown) for connection to a line or cable 26, hinge wire 14, sailing supplies, and cell sliding parts. Line or cable 26, as illustrated in FIG. 1, may be provided to supply energy (e.g., electrical energy). Referring again to FIG. 2, a receiving portion, which may be located between side walls 20, 22, may be configured to receive at least a portion of an ablation element 18. Ablation element 18 may, for example, comprise an ultrasonic transducer or radio frequency (RF) generator, although various other ablation elements may be used. Ablation element 18 may transmit energy (e.g., high intensity focused ultrasound energy) to target tissue. Ablation element 18 may include an emitting surface 28 from which ablation element 18 transmits energy. A controller (not shown) may be provided to control delivery of energy.

Referring again to FIG. 1, each cell 12 may be disposed in a tube or closure chamber 30. Tube 30 may define a single longitudinal channel or lumen. Tube 30 may envelop all or a number of cells 12, including both the cell carrier 16 and the ablation element 18 of each covered cell. A portion of tube 30 that is disposed adjacent the emitting surfaces 28 of the ablation elements 18 may comprise a membrane sufficiently transparent for the energy (e.g., ultrasonic beam) transmitted from the ablation elements 18 to pass through. In some embodiments, the entire tube 30 may comprise a membrane. The membrane may be flexible and elastic and may conform to the required shape to fill the gap between ablation elements 18 and the tissue to be ablated, which can facilitate good acoustic contact between ablation elements 18 and the tissue targeted for ablation. Tube 30 may comprise soft and/or inflammable walls. Tube 30 or a portion of tube 30 (e.g., the membrane or a portion of the membrane) may comprise polyurethane or silicone in an embodiment. In other embodiments, tube 30 or a portion of tube 30 (e.g., the membrane or a portion of the membrane) may comprise another material relatively transparent to ultrasound. In embodiments where a portion of tube 30 (e.g., a portion of the membrane) comprises polyurethane, silicone, or another material relatively transparent to ultrasound, the other portions of tube 30 (e.g., the other portions of the membrane) may comprise different materials. Tube 30 may be permeable in a preferred embodiment, but may also be non-permeable in other embodiments. The use of tube 30 may provide more uniform contact between tube 30 and the surface of the tissue to be ablated, thereby distributing pressure on the tissue more uniformly than conventional devices and facilitating the separation of the emitting surfaces 28 and the membrane of tube 30.

In an embodiment (see FIG. 1), tube 30 may be fed by a fluid inlet 32. Fluid inlet 32 may provide a fluid to the interior of tube 30. The fluid may comprise saline. In other embodiments, the fluid may also comprise any number of other fluids that may be used for cooling. The source of fluid may include a bag that provides a gravity feed and is coupled to the epicardial ablation device with a standard connection such as a standard luer connection. Because fluid is fed to the interior of tube 30, the plurality of cells 12 may be fully or partially immersed in fluid. The fluid flow rate experienced by each cell may be increased using a serial flow configuration as compared to a parallel flow configuration. The increased fluid flow rate may also allow the fluid to circulate more quickly among cells 12, which may result in higher cooling rates by increasing the surface area of the thermal contact. Further, the increased fluid flow may reduce bubbles between the emitting surfaces 28 and the membrane of tube 30, which may further improve reliability and efficiency of the device. Fluid may flow between the emitting surfaces 28 of ablation elements 18 and the membrane of tube 30. The fluid may also serve as a coolant to cool the emitting surfaces 28 of the ablation elements 18. Cells 12 may comprise one or a plurality of apertures 34 (see, e.g., FIG. 2) for facilitating coolant flow proximate ablation element 18.

Tube 30 may be perforated. Accordingly, in an embodiment, tube 30 may have at least one or a plurality of laser holes 36 (see, e.g., FIG. 1) to facilitate coolant flow and to provide a coolant layer between the outer surface of the membrane of tube 30 and the tissue being ablated. At least one laser hole 36 may be disposed proximate to every emitting surface 28 of an ablation element 18 of cell 12 of device 10 in an embodiment. Tube 30 may further include fluid outlet 38. Electrical cable 26, fluid inlet 32, and fluid outlet 38 may, for example, extend through a manipulator that forms a seal with tube 30.

The assembly of cells 12 may be suspended or otherwise positioned in such a way that there is no direct contact between the emitting surfaces 28 of ablation elements 18 and tube 30. For example, in one embodiment, mechanical constraints (e.g., standers 40) may be disposed on one or both of side walls 20, 22 of carrier 16. Standers 40 may be provided to prevent tube 30 from contacting emitting surface 28 of ablation element 18. Stander 40 may be extruded from the edge of cell 12 in an embodiment. In the embodiment where a stander 40 is disposed on only one end of side walls 20, 22 of carrier 16, the opposing side wall of carrier 16 (i.e., without stander 40) may be located adjacent side wall 20, 22 with a stander 40 on an adjacent carrier in order to prevent the emitting surfaces 28 of ablation elements 18 from contacting tube 30. In other embodiments, the tube 30 may be physically attached to the side of the wall 20, 22 and back to make sure that fluid flows between the emitting surface 28 of element 18 and tube 30. Furthermore, fluid pressure inside tube 30 may also prevent tube 30 from contacting emitting surfaces 28 of ablation elements 18.

The device may include a monitoring device to monitor the flow rate of fluid through cells 12. For example and without limitation, the device may include a pressure and/or flow sensor (not shown) to detect a ruptured membrane and/or impeded flow. The pressure and/or flow sensor may be located near fluid outlet 38 in an embodiment. When only a single tube 30 is used through which fluid flows, a single pressure and/or flow sensor may be sufficient to detect a ruptured membrane of tube 30 and/or to sense impeded fluid flow, which improves the reliability of the device.

Additional mechanical constraints (e.g., guides 42) may be disposed on tube 30. Guides 42 may, therefore, be disposed between tube 30 and the back side (i.e., side opposing emitting surface 28) of cells 12 or side walls 20, 22. Guides 42 may be provided to allow cells 12 to be able to move (e.g., slide) relative to tube 30 and/or along the length of tube 30. Guide 42 may be configured to allow each cell 12 to move, for example, approximately one half the length of a cell 12. In other embodiments, guide 42 may be configured to allow each cell 12 to move greater than or less than approximately one half the length of cell 12. When tube 30 is inflated by fluid pressure, each cell 12 attached to each guide 42 may be pulled so that the emitting surface 28 of ablation element 18 of each cell 12 is pulled away from contact with tube 30.

Figure 3:
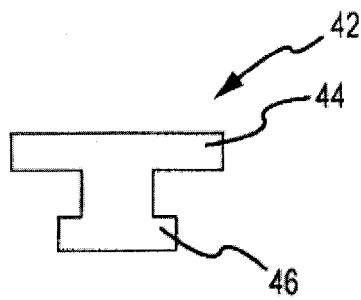
FIG. 3 is a front view of a guide for allowing movement of a cell within a tube of the device of FIG. 1 in accordance with an embodiment of the invention.
Figure 4:
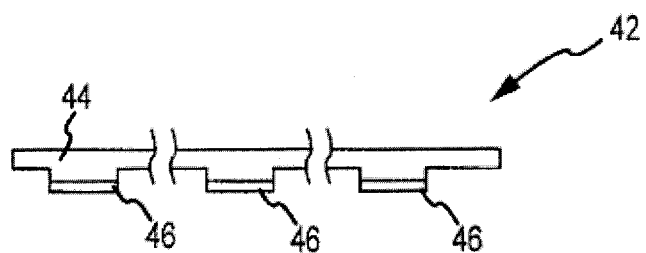
FIG. 4 is a side view of a guide for allowing movement of multiple cells within a tube of the device of FIG. 1 in accordance with an embodiment of the invention.

Referring now to FIG. 3, guide 42 may include a first portion 44 and a second portion 46. First portion 42 may be a continuous portion configured for connection to tube 30. Second portion 46 may be a rail that connects to a cell 12. Rail 46 may be configured to be retained by a cell carrier 16 of a cell 12 to facilitate movement of cell 12 along guide 42. Referring now to FIG. 4, in an embodiment, a single guide 42 may be utilized with multiple rails 46 for facilitating the attachment of multiple cell backs to the single guide 42. In an embodiment, the design may include the configuration where the tube 30 may act as a portion of guide 42. Although FIG. 4 shows three rails 46, fewer or more rails 46 may be utilized on a single guide 42. Guide 42 may comprise a single or dual guide disposed on tube 30. Again, guide 42 may be configured to limit the range of longitudinal motion of the multiple cells 12 to approximately one half of the length of each cell 12.

Figure 5:
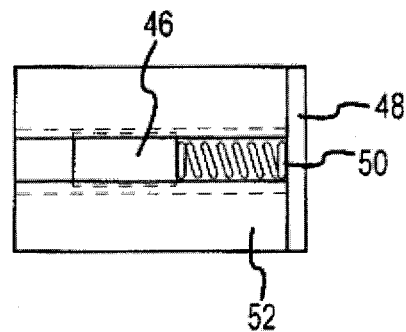
FIG. 5 is a close-up, top view of a guide for allowing movement of a cell within a tube of the device of FIG. 1 in accordance with an embodiment of the invention.

In one embodiment, each cell 12 and/or the assembly (e.g., series) of cells 12 may be vibrated to optimize lesion shaping, including, but not limited to, improved overlap between the ablated regions of adjacent ablation elements 18. For example, the width of the lesion may be increased at and/or near the endocardial side of the myocardium. The movement of cells 12 may be either unidirectional or vibratory (i.e., back and forth). Referring now to FIG. 5, one end of cell 12 at one end of device 10 may include an electromagnetic device 48 and/or spring 50. Electromagnetic device 48 and/or spring 50 may be provided to move one or more cells 12 within tube 30 relative to tube 30 when actuated. Electromagnetic device 48 and/or spring 50 may be disposed above rail 46 or cell 12. In an embodiment, a cell located proximate electromagnetic device 48 and/or spring 50 may be an "active" cell 52 (see FIG. 1 and FIG. 5). Active cell 52 may be moved by electromagnetic device 48 and/or spring 50. When electromagnet 48 is activated, it may, for example, pull active cell 52 toward the electromagnetic device 48. When electromagnet 48 is not activated, the spring force of spring 50 may push active cell 52 away from the electromagnetic device 48. One or more cells 12 of device 10 may comprise "passive" cells 54 (see FIG. 1). Passive cells 54 may be configured to be moved by connection to active cell 52.

Figure 6:
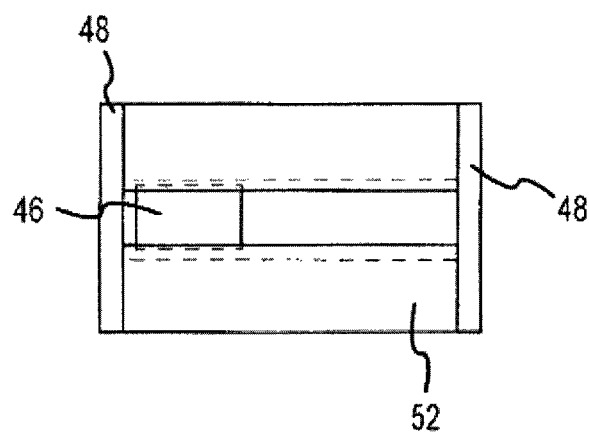
FIG. 6 is a close-up, top view of a guide for allowing movement of a cell within a tube of the device of FIG. 1 in accordance with an embodiment of the invention.

Referring now to FIG. 6, a cell 12 of device 10 may include electromagnetic device 48 at both sides of cell 12, with only one side of the electromagnetic device being active at any given moment. The rail 46 may slide or vibrate in-between to move active cell 52. Cell 12 may thus be bi-stable (e.g., configured for movement between alternative stable positions). A strong magnetic field in a first of the electromagnetic devices, while a weaker field in the second electromagnetic device, may cause the cell 52 to move to a first stable position. A strong magnetic field in a second of the electromagnetic devices, while a weaker field in the first electromagnetic device, may cause the cell 52 to move to a second stable position. One or more cells 12 of device 10 may comprise "passive" cells 54. Passive cells 54 may be configured to be moved through their connection to active cell 52.

Figure 7:
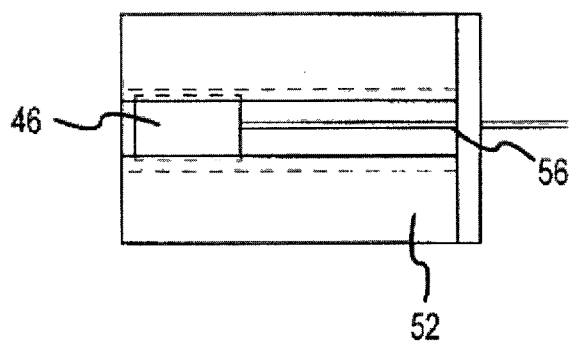
FIG. 7 is a close-up, top view of a guide for allowing movement of a cell within a tube of the device of FIG. 1 in accordance with an embodiment of the invention.

Referring now to FIG. 7, one end cell 12 or rail 46 of device 10 may include a wire 56 instead of an electromagnetic device 48 and/or spring 50 as "active" cell 52 in an embodiment. Wire 56 may also be provided to move one or more cells 12 within tube 30 relative to tube 30. The insert of rail 46 may be sealed at the end and attached to wire 56. Wire 56 may also be disposed above rail 46. An active cell 52 may be moved by pulling wire 56. An active cell 52 may be in a first, initial position. When wire 56 is pulled, active cell 52 (to which wire 56 is connected) is also pulled into a second position. One or more passive cells 54 may be configured to be moved by connection to active cell 52. Electromagnetic device 48 and/or spring 50 and/or wire 56 may comprise means for facilitating movement of an active cell. Passive cell 54 may be connected to active cell 52. Passive cells may therefore be configured to move by its connection to an active cell 52 (e.g., its connection via hinge wire 14). Accordingly, passive cell 54 may be configured to move in correspondence with movement of active cell 52.

The assembly of cells 12 may have a range (e.g., limited range) of movement within tube 30. The assembly of cells may be configured for sliding (e.g., longitudinal) movement within tube 30. The sliding connection between tube 30 and the back of cell 12 (i.e., through use of guide 42, including rail 46) may restrict the motion of each cell to the direction along tube 30. In other words, the guide 42 may only allow motion of cell 12 along the longitudinal direction of tube 30. During ablation, the assembly of cells 12 may by placed (e.g., slid) into different positions relative to tube 30. Accordingly, the assembly of cells may be placed in different positions relative to the tissue to be ablated. During ablation, each cell 12 may send out a sequence of acoustic pulses to ablate the tissue. Acoustic intensity may generally be higher near the center of cell 12, than near its edge or between adjacent cells. Therefore, the heating may also be higher near the center of cell 12, while the heating between the cells may be comparatively less. Insufficient heating may leave ablation gaps between cells 12. By moving cells 12 (e.g., approximately one half of the length of each cell), the ablation gaps may be covered or "filled in," providing more even ablation. The movement of the assembly of cells 12 within tube 30 may thereby provide for a more uniform distribution of the acoustic intensity in the tissue, which can result in more uniform ablation and improved surgical efficiency. Because of the ability to move cells 12 within tube 30, the number of cells 12 utilized in device 10 may be decreased as compared to a conventional device while still being configured to ablate the same amount of tissue. In an embodiment, device 10 may utilize at least one less cell than conventional devices.

When fewer cells are utilized, or even in cases where the same number of cells as a conventional device are utilized, larger gaps may be introduced between adjacent cells. The movement of the assembly of cells 12 within tube 30 may allow ablation elements 18 to be positioned in the areas of the gaps to help ensure that these gaps are acoustically covered. By introducing larger gaps between adjacent cells, the mechanical flexibility of the device may also be improved. In an embodiment, the gap between adjacent cells may be approximately one quarter of the length of a cell 12. In other embodiments, the gap between adjacent cells may be shorter or longer than one quarter of the length of a cell. In an embodiment, there may be gaps between adjacent cells of at least about one quarter of the length of one of the adjacent cells. As described above, each cell 12 may be configured to move approximately one half of the length of each cell 12, so that gaps of approximately one quarter of the length of a cell 12 may be covered through movement of the cells 12.

Although several embodiments of this invention have been described above with a certain degree of particularity, those skilled in the art could make numerous alterations to the disclosed embodiments without departing from the spirit or scope of this invention. All directional references (e.g., upper, lower, upward, downward, left, right, leftward, rightward, top, bottom, above, below, vertical, horizontal, clockwise, and counterclockwise) are only used for identification purposes to aid the reader's understanding of the present invention, and do not create limitations, particularly as to the position, orientation, or use of the invention. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other. It is intended that all matter contained in the above description or shown in the accompanying drawings shall be interpreted as illustrative only and not limiting. Changes in detail or structure may be made without departing from the spirit of the invention as defined in the appended claims.

What is claimed is:

1. A medical device comprising:
   a tissue ablating cell comprising an ablation element; and
   a tube defining a longitudinal lumen and configured to surround and contain said cell, said tube comprising:
   a fluid inlet;
   a fluid outlet; and
   a membrane configured to allow transmission of ablation energy through said membrane, wherein said ablation element is oriented within said tube to direct ablation energy through said membrane to a tissue target,
   wherein said tissue ablating cell is configured for longitudinal movement within said tube.

2. The medical device of claim 1, wherein said ablation element comprises a curved ablation energy emitting surface.

3. The medical device of claim 1, wherein said ablation element emits ablation energy having a frequency of about 10 megahertz.

4. The medical device of claim 1, wherein said longitudinal movement is facilitated by a spring coupled to said tissue ablating cell.

5. The medical device of claim 1, wherein said longitudinal movement is facilitated by an electromagnetic device.

6. The medical device of claim 5, wherein said electromagnetic device is magnetically coupled with said tissue ablating cell.

7. The medical device of claim 5, wherein said electromagnetic device is a first electromagnetic device, further comprising a second electromagnetic device, said first and second electromagnetic devices facilitating said longitudinal movement in opposing directions.

8. The medical device of claim 1, wherein said longitudinal movement is facilitated by a wire coupled to said tissue ablating cell.

9. A medical device comprising:
   a tissue ablating cell comprising an ablation element;
   a tube defining a longitudinal lumen and configured to surround and contain said cell, said tube comprising:
   a fluid inlet;
   a fluid outlet; and
   a membrane configured to allow transmission of ablation energy through said membrane, wherein said ablation element is oriented within said tube to direct ablation energy through said membrane to a tissue target; and
   a guide, extending longitudinally through said tube, to which said tissue ablating cell is coupled, wherein said tissue ablating cell is configured for movement along said guide.

10. The medical device of claim 9, wherein said ablation element is an ultrasound ablation element.

11. The medical device of claim 9, wherein said tissue ablating cell retains a portion of said guide.

12. The medical device of claim 9, wherein said guide is coupled to a portion of said tissue ablating cell that is opposite a direction of transmission of ablation energy of said ablation element.

13. The medical device of claim 9, wherein said tissue ablating cell defines a longitudinal length, and said guide is configured to permit longitudinal movement of said tissue ablating cell of up to about one half of said length.

14. The medical device of claim 9, wherein said tissue ablating cell defines a longitudinal length, and said guide is configured to permit longitudinal movement of said tissue ablating cell of less than about one half of said length.

15. The medical device of claim 9, wherein said tissue ablating cell defines a longitudinal length, and said guide is configured to permit longitudinal movement of said tissue ablating cell of greater than about one half of said length.

16. A medical device comprising:
   a plurality of tissue ablating cells, each comprising a respective ablation element; and
   a tube defining a longitudinal lumen and configured to surround and contain said cells, said tube comprising:
   a fluid inlet;

a fluid outlet; and a membrane configured to allow transmission of ablation energy through said membrane, wherein each said ablation element is oriented within said tube to direct ablation energy through said membrane to a tissue target, wherein each said tissue ablating cell is configured for longitudinal movement within said tube.

17. The medical device of claim 16, wherein said plurality of tissue ablating cells are positioned adjacent each other so as to allow sufficient movement for said tube to be formed in an annular shape.

18. The medical device of claim 16, wherein movement of two or more of said plurality of cells is facilitated by an electromagnetic device coupled to a first of said two or more of said plurality of cells.

19. The medical device of claim 16, wherein movement of two or more of said plurality of cells is facilitated by a spring coupled to a first of said two or more of said plurality of cells.

20. The medical device of claim 16, wherein movement of two or more of said plurality of cells is facilitated by a wire coupled to a first of said two or more of said plurality of cells.

* * * * *